(12) United States Patent
Delbeke et al.

(10) Patent No.: US 10,596,370 B2
(45) Date of Patent: Mar. 24, 2020

(54) DEVICE FOR ELECTROCHEMICALLY RELEASING A COMPOSITION IN A CONTROLLED MANNER

(71) Applicants: SORIN CRM SAS, Clamart (FR); UNIVERSITÉ CATHOLIQUE DE LOUVAIN, Louvain-la-neuve (BE)

(72) Inventors: Jean Delbeke, Kraainem (BE); Sophie Demoustier-Champagne, Bossiere (BE); Vincent Callegari, Louvain-la-Neuve (BE); Lucas Leprince, Brussels (BE); Benoit Gerard, Dion-le-Mont (BE)

(73) Assignees: SORIN CRM SAS, Clamart (FR); UNIVERSITÉ CATHOLIQUE DE LOUVAIN, Louvain-la-neuve (BE)

( * ) Notice: Subject to any disclaimer, the term of this patent is extended or adjusted under 35 U.S.C. 154(b) by 0 days.

(21) Appl. No.: 16/219,366

(22) Filed: Dec. 13, 2018

(65) Prior Publication Data
US 2019/0255320 A1   Aug. 22, 2019

Related U.S. Application Data

(63) Continuation of application No. 14/430,869, filed as application No. PCT/EP2012/068891 on Sep. 25, 2012, now abandoned.

(51) Int. Cl.
*C25B 15/02*  (2006.01)
*C25B 9/00*  (2006.01)
(Continued)

(52) U.S. Cl.
CPC ............... *A61N 1/306* (2013.01); *A61N 1/04* (2013.01); *A61N 1/05* (2013.01); *A61N 1/32* (2013.01)

(58) Field of Classification Search
CPC . A61N 1/04; A61N 1/05; A61N 1/306; A61N 1/32
(Continued)

(56) References Cited

U.S. PATENT DOCUMENTS

| 4,585,652 A | 4/1986 | Miller et al. |
| 4,822,339 A | 4/1989 | Tran |

(Continued)

FOREIGN PATENT DOCUMENTS

| WO | WO-2009/050168 A1 | 4/2009 |
| WO | WO-2012/050876 | 4/2012 |

OTHER PUBLICATIONS

Evans et al., Promoting neurite outgrowth from spiral ganglion neuron explants using polypyrrole/BDNF-coated electrodes, J Biomed Mater Res A. Oct. 2009;91(1):241-50, 10 pages.

(Continued)

*Primary Examiner* — Zulmariam Mendez
(74) *Attorney, Agent, or Firm* — Foley & Lardner LLP (57) ABSTRACT

According to a first aspect, the invention relates to a device (10) for electrochemically releasing a composition and comprising: one working electrode (30) comprising an electroactive conjugated polymer (40) containing or doped with said composition, a counter electrode (50), and a reference electrode (60). The device (10) is characterized in that it comprises electrical means (95, 100; 320; 165, 180) connected to the working electrode (30) and to the counter electrode (50) for obtaining at said working electrode (30) at least one composition releasing sequence (65) with respect to said reference electrode (60), each composition releasing sequence (65) comprising: a first voltametric pulse (70), followed by a rest period (80) during which no current is able to flow through said working electrode (30), followed by a second voltametric pulse (90), followed by an inter-
(Continued)

mediate period (160) during which no current is able to flow through said working electrode (30).

15 Claims, 7 Drawing Sheets (51) Int. Cl.
*A61N 1/30* (2006.01)
*A61N 1/04* (2006.01)
*A61N 1/05* (2006.01)
*A61N 1/32* (2006.01)

(58) Field of Classification Search
USPC .................................................... 204/230.2
See application file for complete search history.

(56) References Cited

U.S. PATENT DOCUMENTS

| | | | |
|---|---|---|---|
| 5,422,246 | A | 6/1995 | Koopal et al. |
| 6,748,954 | B2 | 6/2004 | Lee et al. |
| 2009/0012446 | A1 | 1/2009 | Cui et al. |
| 2011/0270152 | A1 | 11/2011 | Atanasoska et al. |

OTHER PUBLICATIONS

International Search and Written Opinion for PCT Application No. PCT/EP2012/068891, dated Jun. 5, 2013, 13 pages.

DEVICE FOR ELECTROCHEMICALLY RELEASING A COMPOSITION IN A CONTROLLED MANNER

CROSS-REFERENCE TO RELATED APPLICATIONS

This application is a continuation of U.S. patent application Ser. No. 14/430,869, filed Mar. 24, 2015, which is a 371 U.S. National Application of International Application No. PCT/EP2012/068891, filed Sep. 25, 2012 both of which are incorporated herein by reference in their entirety.

FIELD OF THE INVENTION

According to a first aspect, the invention relates to a device for a controlled electrochemical release of a composition. Preferably, this device is implantable. According to a second aspect, the invention relates to a method for a controlled electrochemical release of a composition.

DESCRIPTION OF PRIOR ART

The active control of the release of a composition, in terms of time, quantity and accuracy of delivery, remains a big challenge. For example in the case of medical applications, the strategy of substance local delivery is really promising in comparison with systemic drug taking. Therefore, controlled release of a composition or drug has become an important mode of treatment for various diseases. A release rate of such methods can be controlled mechanically for example, as it is the case in the U.S. Pat. No. 6,748,954. Alternatively, electrochemical methods can be used as explained for instance in the U.S. Pat. Nos. 5,422,246, 4,585,652 or in the patent application WO2009/050168. As known by the one skilled in the art, electrochemical methods typically use an electrode coated with an electroactive conjugated polymer containing or doped with a composition. This composition, bound to the polymer, is present as ionic charge to compensate the charge of the polymeric backbone, so it ensures the polymer electroneutrality. Upon electrical stimulation, the composition can be released as the conjugated polymer can be electrically switched between an oxidized and a reduced state as an example: the electroactive conjugated polymer is in an oxidized state when containing the composition, whereas it passes in a reduced state (by the application of a negative voltage to the electrode covered by the electroactive conjugated polymer) when the composition has been released.

In the U.S. Pat. No. 4,585,652, a polymer (polypyrrole for instance) containing a composition (glutamate for instance) has been deposited on an electrode to form a film. A voltage time square wave was then applied to the film between two limits of opposite polarity. Hence, the square wave comprises voltametric pulses of opposite polarity. For a value of a given polarity of these voltametric pulses, the polymer is reduced and for the other one, it is oxidized. When the film is reduced, release of the composition takes place. The system proposed in this U.S. Pat. No. 4,585,652 presents some drawbacks. After a release of a composition because of the application of a reduction pulse for instance, this composition can immediately be re-attracted to the polymer film because of the application of an oxidation pulse that follows. Hence, the composition cannot efficiently diffuse towards a zone to be treated. In other words, the system of U.S. Pat. No. 4,585,652 lacks efficiency. Second, the pulses of the potential time square wave (of positive or negative polarity) have a rather long duration. In the examples given in this patent, these pulses are applied between a time equal to or longer than 1 s. When applied to living tissues, such long voltage pulses can lead to undesirable activation of excitable tissues close to the electrode comprising the polymer.

In the publication entitled "Promoting neurite outgrowth from spiral ganglion neuron explants using polypyrrole/BDNF-coated electrodes" by Evans A J et al. and published in J Biomed Mater Res A. 2009 October; 91(1):241-50, another system is proposed for delivering a composition contained in a polymer deposited on an electrode. As shown in FIG. 1(b) of this article, an electrode covered by a polymer containing a composition is subjected to biphasic current pulses. Between two current pulse phases, there is a 25 μs open-circuit pulse interphase gap. Such a gap is not described in the U.S. Pat. No. 4,585,652. Between biphasic current pulses, there is a short-circuit phase (having a duration of around 3.78 ms). Such a system does not allow one to have a good and precise control on the quantity of composition that is released. In particular, due to typical inhomogeneous ionic concentration, this short-circuit will allow the release of the composition to go on according to an uncontrolled manner, when no release of the composition is normally wanted. Also, there is a 'burst' of release of the composition during the first day, even when no electrical stimulation is applied as shown in FIG. 2(a) of the above mentioned paper.

SUMMARY OF THE INVENTION

According to a first aspect, it is an object of the present invention to provide a device for electrochemically releasing a composition with a higher control of the quantity and timing of the released composition. To this end, the device of the invention comprises:

at least one working electrode comprising an electroactive conjugated polymer containing or doped with said composition;
a counter electrode;
a reference electrode;

characterized in that said device further comprises:

electrical means connected to the at least one working electrode and to the counter electrode for obtaining at said at least one working electrode at least one composition releasing sequence with respect to said reference electrode, each composition releasing sequence comprising:

a first voltametric pulse for releasing said composition, having a first voltage, a first polarity and a first duration, followed by a rest period during which no current is able to flow through said working electrode, followed by a second voltametric pulse for replacing said composition with at least one ion, having a second voltage, a second polarity opposite to said first polarity and a second duration, followed by an intermediate period during which no current is able to flow through said at least one working electrode, at the end of which another composition releasing sequence may be applied.

Preferably, the composition that is released is a therapeutic composition.

The device of the invention is advantageous in that it comprises electrical means for applying a controlled signal to the at least one working electrode such that at least one composition releasing sequence as defined above can be obtained at the working electrode with respect to the reference electrode. Such electrical means allow a higher control of the quantity and timing of the released composition. Indeed, electrochemical release is determined by the effective voltage. Hence, the device of the invention is more precise. The electrical means can comprise for instance a generator, a battery, a switch or a combination of any of such elements. The electrical means can comprise any other devices suitable for obtaining voltametric pulses at the working electrode with respect to the reference electrode. These electrical means allow obtaining that no current is able to flow through the working electrode during the rest period and during an intermediate period between composition releasing sequences contrary to what is explained in page 243 of Evans A J et al.'s publication. This ensures that no activation of the electroactive conjugated polymer allowing a release of the composition takes place when it is not desired. Hence, the device of the invention provides a higher control of the quantity and timing of the released composition. By using the device of the invention, there is no 'burst' of release of the composition during the first day if no biphasic voltage pulse is applied to the working electrode. During the rest period, no current is able to flow through the working electrode. This allows the composition to diffuse efficiently towards and/or into a zone to be treated (zone of interest) contrary to the system of U.S. Pat. No. 4,585,652. Preferably, the device of the invention is rechargeable. Hence, in such a preferred embodiment, it is possible to recharge the electroactive conjugated polymer with a composition.

Preferably, the electrical means comprise a voltage source and a switch connected between the working and the counter electrodes. Preferably, the electrical means comprise a current source connected between the working and the counter electrodes.

When a current source is used, its very large internal impedance (this internal impedance tends to infinity in an ideal case), ensures that no current is able to flow through the working electrode when a controller associated with the current source imposes zero current.

Preferably, the rest period has a duration comprised between 35 µs and 10 ms. Such a preferred duration allows increasing the efficiency of the release of the composition.

Preferably, the device of the invention further comprises determination means for determining a quantity of flowing electrical charges through the working electrode during the first and second voltametric pulses. Then, the device of the invention allows determining a quantity of composition that is released. Indeed, the released composition comprises ions in methods of electrochemical release. Therefore, by determining the quantity of flowing electrical charges through the working electrode during the first voltametric pulse, one can determine and control the quantity of released composition. The determination means can comprise for instance an ammeter for measuring an electrical current between the working and the counter electrode during the first and second voltametric pulse. The determination means can also comprise for instance a time integrator for determining the first duration of the first voltametric pulse. Then, by integrating the electrical current flowing through the working electrode, one can determine the flowing electrical charges through the working electrode during the first voltametric pulse, and finally the quantity of composition that is released during the first duration of the first voltametric pulse. Hence, in this preferred embodiment, the device of the invention further allows determining a quantity of released composition. As an illustrative example, it can be estimated from the electrochemical equations that 1 ms pulses could release about 1 pg Dexamethasone from a 0.1 $mm^2$ working electrode at −0.45 V relative to a silver/silver chloride reference electrode. By comparing the quantity of flowing electrical charges through the working electrode during the first and second voltametric pulses, one can check that electro-neutrality is respected. Such an aspect is of primary importance for biocompatibility reasons when the device is implantable according to a preferred embodiment.

Preferably, the device of the invention further comprises control means for adapting the first duration of the first voltametric pulse for allowing the device to release a preset quantity of composition. Such control means can include for instance a computer or any control unit. Other devices are possible. By controlling the first duration of the first voltametric pulse, it is possible to deliver a preset quantity of composition.

Preferably, the device of the invention comprises control means for automatically determining and adapting the second duration of the second voltametric pulse from a quantity of flowing electrical charges through the working electrode during the first voltametric pulse. This preferred embodiment has the advantage of allowing a control of the electro-neutrality. Such an aspect is of primary importance for biocompatibility reasons when the device is implantable. Preferably, this quantity of flowing electrical charges through the working electrode during the first voltametric pulse is determined by the determination means.

Preferably, Silver or silver choride are used as a material for the reference, working and counter electrodes. However, Silver or silver choride are toxic and are thus preferably not used for implantable electrodes for in-vivo applications. Preferably, for implantation applications, biocompatible stable materials such as platinum, platinum-iridium, platinum coated with iridium, iridium, gold, chromium, carbon, stainless steel can be used for the reference, working and counter electrodes. Preferably, these three electrodes are made of a material such that they are characterized by a stable electrochemical potential in implanted conditions.

Preferably, the first polarity of the first voltametric pulse is negative with respect to the reference electrode when the composition comprises negatively charged ions. In another preferred embodiment, the first polarity of the first voltametric pulse is positive with respect to the reference electrode when the composition comprises positively charged ions.

Preferably, the device of the invention is implantable in a mammal body. Then, the first duration of the first voltametric pulse is preferably such that it prevents the first voltametric pulse from inducing a stimulation of nerves and/or living tissues. Preferably, the first duration of the first voltametric pulse is equal to or shorter than 1 s. Such a small duration induces that a small quantity of electric charges is delivered during the first voltametric pulse. As a consequence, the risk of activating tissues surrounding the working electrode is avoided or strongly limited when using the device of the invention in-vivo.

In another preferred embodiment, the device of the invention comprises stimulation means able to produce at the working electrode an output appropriate for stimulating nerves or living tissues. Hence, according to this preferred embodiment, the device of the invention is able to release a composition and to stimulate nerves or living tissues. Preferably, said stimulation means are able to produce at the working electrode an output appropriate for stimulating nerves or living tissues when the composition is totally released.

According to a second aspect, the invention relates to a method for a controlled electrochemical release of a composition from at least one working electrode comprising an electroactive conjugated polymer containing or doped with said composition, said method comprising the step of imposing between the at least one working electrode and a counter electrode specific electrical conditions for obtaining at said at least one working electrode at least one composition releasing sequence with respect to a reference electrode, each composition releasing sequence comprising:

i) a first voltametric pulse for releasing said composition and having a first voltage, a first duration and a first polarity, followed by ii) a rest period during which no current is able to flow through said working electrode, followed by iii) a second voltametric pulse for replacing said composition with at least one ion having a second voltage, a second duration and a second polarity opposite to the first polarity, followed by iv) an intermediate period during which no current is able to flow through said at least one working electrode, at the end of which another composition releasing sequence may be applied.

Examples of specific electrical conditions are: an open-circuit configuration between the working and the counter electrodes during the rest and intermediate periods by using a switch connected between these two electrodes; imposing that no current is able to flow through the working electrode during the rest and intermediate periods by using a current source with a zero-current setting point during these periods; tuning the electrical current flowing through the working electrode during steps i) and iii) in order to obtain the first and the second voltametric pulses.

Preferably, a quantity of electrical charges flowing through said working electrode during step i) is determined. Then, the quantity of composition that is released can be determined.

More preferably, a quantity of electrical charges flowing through said working electrode during step iii) is also determined. Then, electro-neutrality can be checked by comparing the quantity of electrical charges flowing through the working electrode during steps i) and iii).

Preferably, the number of composition releasing sequences is adapted for releasing a preset quantity of composition. More preferably, the frequency of composition releasing sequences is adapted for releasing a quantity of composition at a preset rate.

SHORT DESCRIPTION OF THE DRAWINGS

These and further aspects of the invention will be explained in greater detail by way of example and with reference to the accompanying drawings in which.

The figures are not drawn to scale. Generally, identical components are denoted by the same reference numerals in the figures.

DETAILED DESCRIPTION OF PREFERRED EMBODIMENTS

Definitions

The term "composition" as used herein is a set composed of various substances whose quantities are controlled, preferably biocompatible substances.

The term voltametric pulse as used herein is defined as a pulse of given voltage and given duration between a working 30 and a reference 60 electrodes, resulting from a voltage pulse or current pulse actively applied between working 30 and counter 50 electrodes. The working electrode current is preferably determined in order to quantify the amount of charges exchanged.

The term "composition releasing sequence" as used herein has a first voltametric pulse 70, followed by a rest period 80 during which no current is able to flow through the working electrode (or corresponding to a zero current phase through the working electrode 30), followed by a second voltametric pulse 90 of opposite polarity, followed by a intermediate period 160 during which no current is able to flow through the working electrode (or corresponding to a zero current phase through the working electrode 30), until a possible next composition releasing sequence 65.

The terms 'no current is able to flow through the working electrode' (during the rest and intermediate periods), means that the current flowing through said working electrode is then equal to or lower than 100 nA.

The term 'doped' means that there is an interaction, for instance an ionic or covalent binding, between the electroactive conjugated polymer 40 and the composition.

The term 'contains' means that the composition is simply contained in the electroactive conjugated polymer 40: it refers to the amount of composition that has no direct interaction with the electroactive conjugated polymer 40.

The term "electroactive conjugated polymer" 40 refers to a polymer which has the ability to undergo reversible redox reaction when a voltage is applied to them. Such conjugated polymers 40 can be for instance polymers or copolymers based on heterocycle moiety as monomers, aniline and substituted aniline derivatives, cyclopentadiene and substituted cyclopentadiene derivatives, phenylene or substituted phenylene derivatives, pentafulvene and substituted pentafulvene derivatives, acetylene and substituted acetylene derivatives, indole and substituted indole derivatives, carbazole and substituted carbazole derivatives. Such conjugated polymers can also be compounds based on formula (I) and (II) shown at FIG. 4, wherein n is an integer greater than 1, 2, 3, 4, or 5, or ranges from 1 to 1000, 5 000, 10 000, 100 000, 200 000, 500 000 or 1 000 000 or higher, X is selected from the group consisting of —NR$^1$—, O, S, PR$^2$, SiR$^5$R$^6$, Se, AsR$^3$, BR$^4$ wherein R and R' which can be identical or not are independently selected from the group consisting of, alkyl, aryl, hydroxyl, alkoxy; or R and R' together with the carbon atoms to which they are attached form a ring selected from aryl, heteroaryl, cycloalkyl, heterocyclyl;

R$^1$, R$^2$, R$^3$, R$^4$, R$^5$ and R$^6$ are independently selected from the group consisting of hydrogen, alkyl or aryl group;

A and A' can be independently selected from the group consisting of heterocycle, heterocyclyl, alkenyl, alkynyl or aromatic ring and wherein A and A' can be identical or not.

The term copolymers as used herein refers to polymers derived from at least two different monomeric species. Copolymers can be alternating, periodic, statistical, random or block copolymers.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$ alkyl means an alkyl of one to four carbon atoms. $C_{1-6}$ alkyl includes all linear, or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers.

The term "aryl" as used herein refers to a polyunsaturated, aromatic hydrocarbyl group having a single ring (i.e. phenyl) or multiple aromatic rings fused together (e.g. naphtyl), or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7- or 8-azulenyl, naphthalen-1- or -2-yl, A-, 5-, 6 or 7-indenyl, 1- 2-, 3-, 4- or 5-acenaphtylenyl, 3-, 4- or 5-acenaphtenyl, 1-, 2-, 3-, 4- or 10-phenanthryl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl. The aryl ring can optionally be substituted by one or more substituent(s). An "optionally substituted aryl" refers to an aryl having optionally one or more substituent(s) (for example 1 to 5 substituent(s)), for example 1, 2, 3 or 4 substituent(s) at any available point of attachment selected independently in each incidence. Unless provided otherwise, non-limiting examples of such substituents are selected from halogen, hydroxyl, oxo, nitro, amino, cyano, alkyl, cycloalkyl, alkenyl, alkynyl, cycloalkylalkyl, $C_{1-4}$alkylamino, $C_{1-4}$alkylamino, alkoxy, aryl, heteroaryl, arylalkyl, haloalkyl, haloalkoxy, alkoxycarbonyl, alkylcarbamoyl, heteroarylalkyl, alkylsulfonamide, heterocyclyl, alkylcarbonylaminoalkyl, aryloxy, alkylcarbonyl, acyl, arylcarbonyl, carbamoyl, alkylsulfoxide, alkylcarbamoylamino, sulfamoyl, N—$C_{1-4}$-alkylsulfamoyl or N, N—$C_{1-4}$ dialkylsulfamoyl, —SO$_2$R$^C$, alkylthio, carboxyl, and the like, wherein R$^C$ is $C_{1-4}$alkyl, haloalkyl, $C_{3-6}$cycloalkyl, $C_{1-4}$alkylsulfonamido or optionally substituted phenylsulfonamido.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno [2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1 (2H)-yl, 6-oxopyrudazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "cycloalkyl" as used herein is a cyclic alkyl group, that is to say, a monovalent, saturated, or unsaturated hydrocarbyl group having 1 or 2 cyclic structure. Cycloalkyl includes all saturated hydrocarbon groups containing 1 to 2 rings, including monocyclic or bicyclic groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, with cyclopropyl being particularly preferred. An "optionally substituted cycloalkyl" refers to a cycloalkyl having optionally one or more substituent(s) (for example 1 to 3 substituent(s), for example 1, 2 or 3 substituent(s)), selected from those defined above for substituted alkyl. When the suffix "ene" is used in conjunction with a cyclic group, this is intended to mean the cyclic group as defined herein having two single bonds as points of attachment to other groups.

The terms "heterocyclyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituent(s) (for example 1 to 4 substituent(s), or for example 1, 2, 3 or 4 substituent(s)), selected from those defined above for substituted aryl. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "alkenyl" as used herein refers to an unsaturated hydrocarbyl group, which may be linear, branched or cyclic, comprising one or more carbon-carbon double bonds. Alkenyl groups thus comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like. An optionally substituted alkenyl refers to an alkenyl having optionally one or more substituent(s) (for example 1, 2 or 3 substituent(s), or 1 to 2 substituent(s)), selected from those defined above for substituted alkyl.

The term "alkynyl" as used herein, similarly to alkenyl, refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers and the like. An optionally substituted alkynyl refers to an alkynyl having optionally one or more substituent(s) (for example 1 to 4 substituent(s), or 1 to 2 substituent(s)), selected from those defined above for substituted alkyl.

PREFERRED EMBODIMENTS

Figure 1:
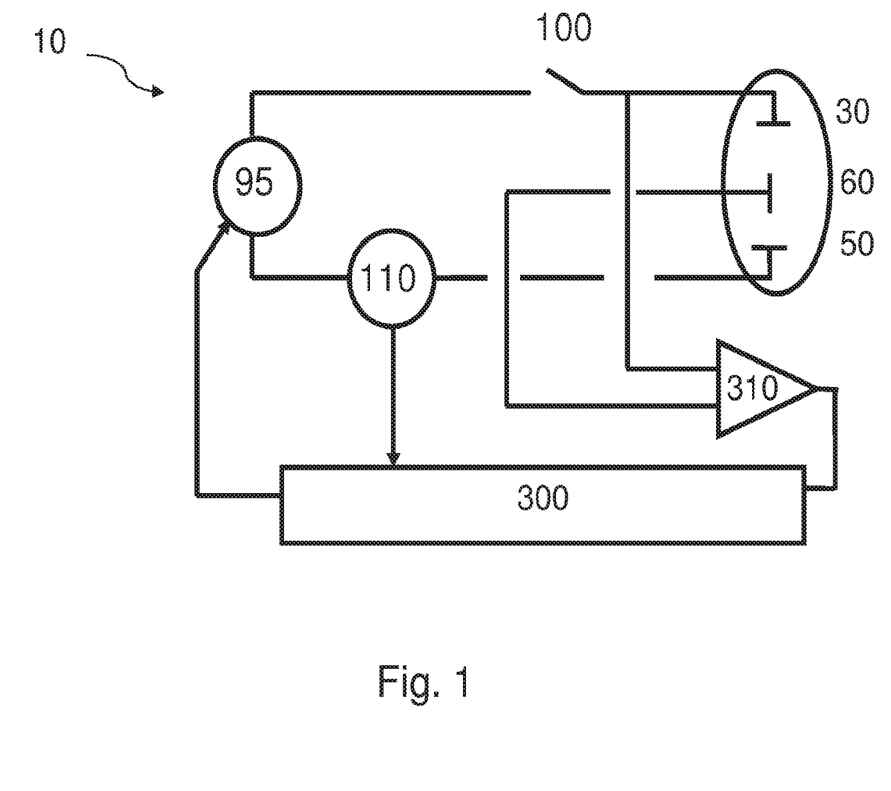
FIG. 1 schematically shows a preferred embodiment of the device of the invention where the electrical means comprise a voltage source and a switch connected between the working and the counter electrodes.

FIG. 1 shows a preferred embodiment of a device 10 according to a first aspect of the invention. This device 10 comprises a working electrode 30, a counter electrode 50 and a reference electrode 60. The working electrode 30 comprises an electroactive conjugated polymer 40 (not shown in FIG. 1) that contains or that is doped with a composition. Even if it is preferred to have a three electrodes configuration (comprising the working 30, counter 50, and reference 60 electrode), one could use the device 10 of the invention with only two electrodes. In this case, the counter 50 and reference 60 electrodes are identical. Nevertheless, as known by the one skilled in the art, a reference electrode 60 is preferably an electrode with zero current. Counter electrode 50 is sometimes named current drain by the one skilled in the art.

In the preferred embodiment shown in FIG. 1, electrical means for obtaining at the working electrode 30 at least one composition releasing sequence 65 comprise a voltage source 95 and a switch 100 connected between the working 30 and the counter 50 electrodes. As shown in FIG. 1, the voltage source 95 is preferably adjusted through a controller 300 so that the voltage between working 30 and reference 60, measured by amplifier 310, reaches the preset level of the voltametric pulses (70 and 90). Preferably, an ammeter 110 connected to the controller 300 allows one to measure the electric current flowing through the working electrode 30, and so the delivered quantity of electric charges during the first 70 and/or second 90 voltamectric pulses. Preferably, the controller 300 is able to control the switch 100 and the electric charges balance between first 70 and second 90 voltametric pulses. The switch 100 allows imposing that no current is able to flow through the working electrode 30 during the rest period 80 and during an intermediate period 160 between two composition releasing sequences 65.

Figure 2:
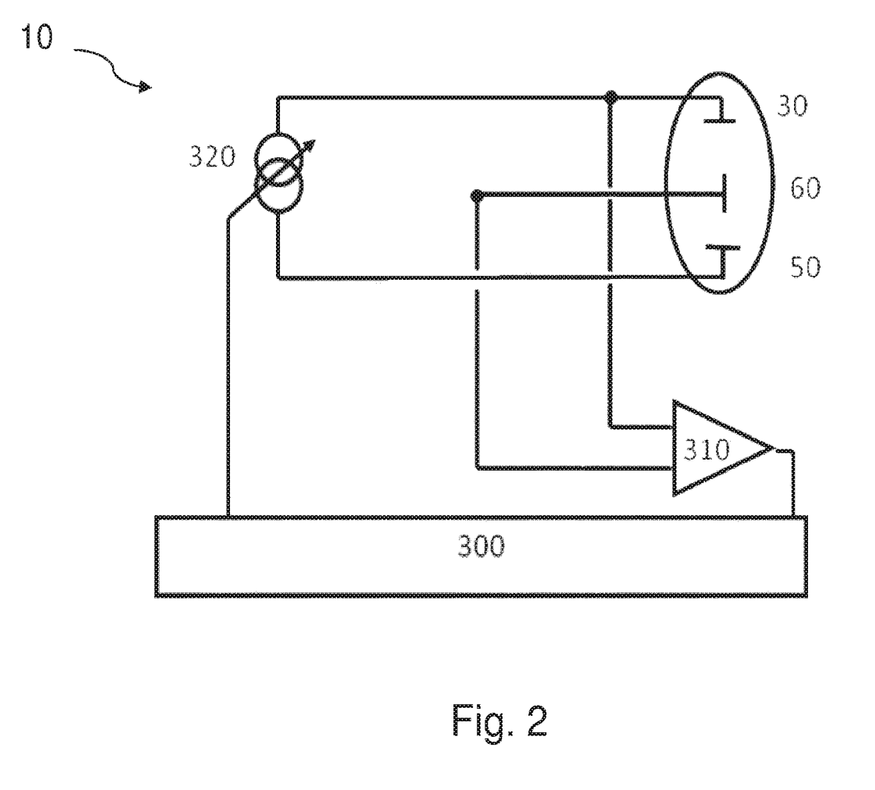
FIG. 2 schematically shows another preferred embodiment of the device of the invention where the electrical means comprise a current source connected between the working and the counter electrodes.

FIG. 2 schematically shows another preferred embodiment of the device 10 of the invention when the electrical means comprise a current source 320 for obtaining at the working electrode 30 the at least one composition releasing sequence 65. In this case, the controller 300 continuously adjusts the electrical current provided by the current source 320 in order to induce an electric voltage between the working 30 and the reference electrode 60 that follows a desired preset voltametric pulse amplitude and duration. In this case, no switch 100 is necessary. As shown in FIG. 2, the electric voltage between the working 30 and the reference 60 electrodes is preferably provided to a controller 300 by the intermediate of an amplifier 310. The controller 300 and the current source 320 are able to impose that no current is able to flow through the working electrodes 30 (in particular during the rest 80 and the intermediate 160 periods) as a current source has a very large internal impedance (this internal impedance tends to infinity for an ideal current source when current output is set to zero). Hence, the controller 300 and the current source 320 allow obtaining rest 80 and intermediate 160 periods during which no current is able to flow through the working electrode 30.

Figure 3:
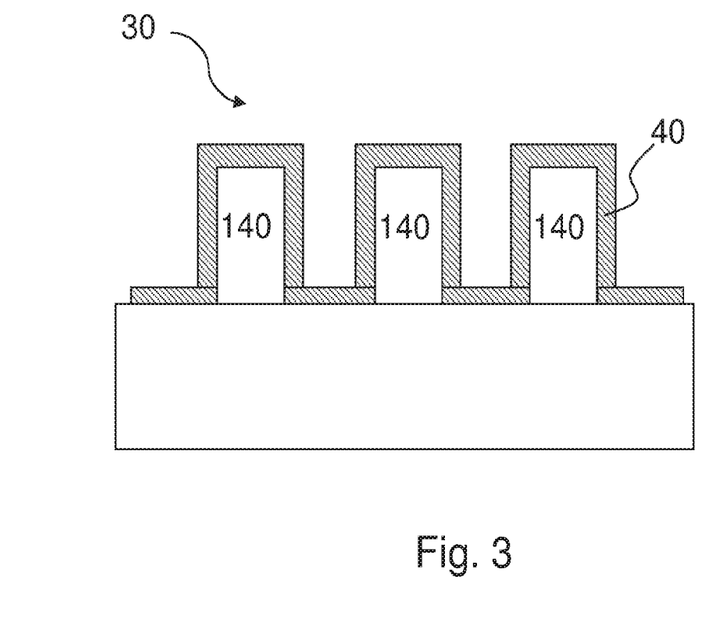
FIG. 3 shows a preferred embodiment for the working electrode of the device of the invention.

Upon electrical stimulation of the working electrode 30, the composition can be released. The working electrode 30 is electrically connected to electrical means capable of charging and discharging the electroactive conjugated polymer 40. More precisely, these electrical means are able to apply a controlled signal to the working electrode 30 in order to obtain at the working electrode 30 at least one composition releasing sequence 65 with respect to the reference electrode 60. In the simplified illustrations of FIGS. 1 and 2, these electrical means are represented by either (FIG. 1) a voltage source 95 and a switch 100 that are connected in series to the working electrode 30, either (FIG. 2) a current source 320. Preferably, these electrical means are coupled to a controller 300. The voltage source 95 is also electrically connected to the counter electrode 50 in the example shown in FIG. 1. Preferably, the device 10 of the invention also includes determination means 110. These determination means 110 are able to determine a quantity of flowing electrical charges between the working 30 and the counter 50 electrode during the first voltametric pulse 70. Preferably, the determination means 110 are also able to determine a quantity of flowing electrical charges between the working 30 and the counter 50 electrodes during the second voltametric pulse 90. Preferably, the determination means 110 comprise an ammeter, for measuring an electrical current between the working 30 and the counter 50 electrodes, and a time integrator for determining the first duration of the first voltametric pulse 70. Preferably, such a time integrator is also able to determine the second duration of the second voltametric pulse 90. In a preferred embodiment, the three electrodes (30, 50 and 60) are in contact with a physiological medium such as spinal fluid, lymph, nerve, muscle or any other tissue as an example. In a preferred use, the three electrodes (30, 50 and 60) are implanted in a mammal body for releasing a composition in vivo. Preferably, the working electrode 30 is coated with the electroactive conjugated polymer 40 and the working 30, counter 50 and reference 60 electrodes are made of platinum or of any biocompatible noble metal or metal combination that can provide a stable potential reference in a mammal body. In a preferred embodiment, the working electrode 30 comprises nanoscopic sized electrically conducting surface microstructures 140 coated by the electroactive conjugated polymer 40 containing the composition as shown in FIG. 3.

Electrochemical release of a composition is notably described in the patent application WO2009/050168 and is known by the one skilled in the art. In a preferred embodiment, the electroactive conjugated polymers 40 are based on heterocycle moiety as monomers such as pyrrole and substituted pyrrole derivatives, furan and substituted furan derivatives, thiophene and substituted thiophene derivatives, phosphole and substituted phosphole derivatives, silole and substituted silole derivatives, arsole and substituted arsole derivatives, borole and substituted borole derivatives, selenole and substituted selenole derivatives or aniline and substituted aniline derivatives. In a preferred embodiment, the conjugated polymers are based on pyrrole and substituted pyrrole derivatives. This list in not exhaustive. Electroactive conjugated polymer 40 can also be a compound based on formula (I) and (II) of FIG. 4.

The electroactive conjugated polymer 40 of the device 10 of the invention may also be combined with or doped with a composition such as for example a therapeutic composition or a drug, which, according to the invention, shall be locally released upon further electrical stimulation. The composition may comprise natural compounds, or biological molecules of interest. Natural compounds may be vitamins. Biological molecules may be nucleic acids such as nucleotides, oligonucleotides, antisense oligonucleotides. DNA, RNA and mRNA; amino acids and natural, synthetic and recombinant proteins, glycoproteins, polypeptides, peptides, enzymes; antibodies, hormones, cytokines and growth factors. The composition may comprise chemical molecules. Preferably, the composition comprises one or more anticancer drugs, antipsychotic, antiparkinsonian agents, antiepileptic agents, antimigraine agents. The electroactive conjugated polymer 40 of the device 10 of the invention is preferably doped with a composition or drug that can be locally released upon further electrical stimulation. The composition may comprise bioactive molecules of interest including, for example, nutritional substances such as vitamins; active compounds such as anticancer drugs, antipsychotic, antiparkinsonian agents, antiepileptic agents, antimigraine agents; nucleic acids such as nucleotides, oligonucleotides, antisense oligonucleotides, DNA, RNA and mRNA; amino acids and natural, synthetic and recombinant proteins, glycoproteins, polypeptides, peptides, enzymes; antibodies, hormones, cytokines and growth factors. Preferably, the composition comprises one or more antiinflammatory agents. More preferably, the composition comprises one or more anti-TNF-alpha agents such as adalimumab, infliximab, etanercept, certolizumab pegol, and golimumab; one or more steroidal anti-inflammatory agents such as dexamethasone disodium; one or more non-steroidal anti-inflammatory agents like aceclofenac, acemetacin, aspirin, celecoxib, dexibuprofen, dexketoprofen, diclofenac, diflunisal, etodolac, etoricoxib, fenbrufen, fenoprofen, flurbiprofen, ibuprofen, indomethacin, ketoprofen, ketorolac trometamol, lumiracoxib, mefanamic acid, meloxicam, nabumetone, naproxen, nimesulide, oxaprozin, parecoxib, phenylbutazone, piroxicam, proglumetacin, sulindac, tenoxicam, and tiaprofenic acid.

Figures 4, 5:
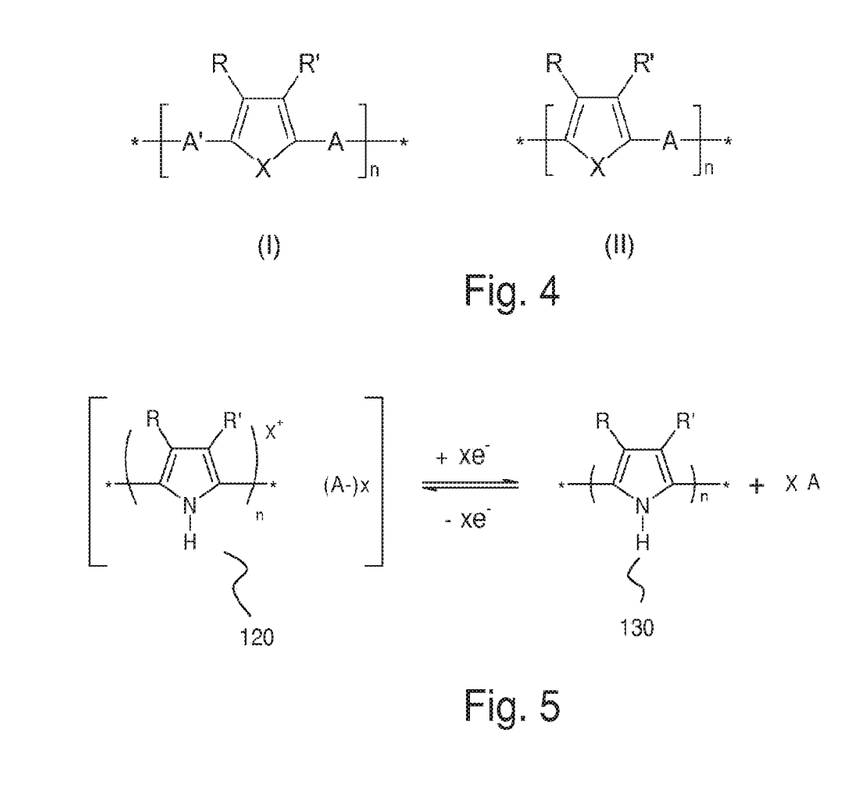
FIG. 4 shows an example of monomer units for the electroactive conjugated polymer.
FIG. 5 shows the principle of electrochemical release (or redox process) of a composition that is contained in an electroactive conjugated polymer.

FIG. 5 schematically shows the principle of electrochemical release (or redox process) of a composition that is contained in an electroactive conjugated polymer 40. More precisely, FIG. 5 depicts the redox process at the basis of release of a composition (A−), where polypyrrole (electroactive conjugated polymer 40) in an oxidized conductive form 120 is shown converting to polypyrrole in a neutral form 130 after electrical stimulation. 'A−' represents hydrated ions (the composition) and 'x' the oxidation state of pyrrole unit in polypyrrole. In the example shown in FIG. 5, release of the composition is induced by reduction of the electroactive conjugated polymer 40.

Figure 6:
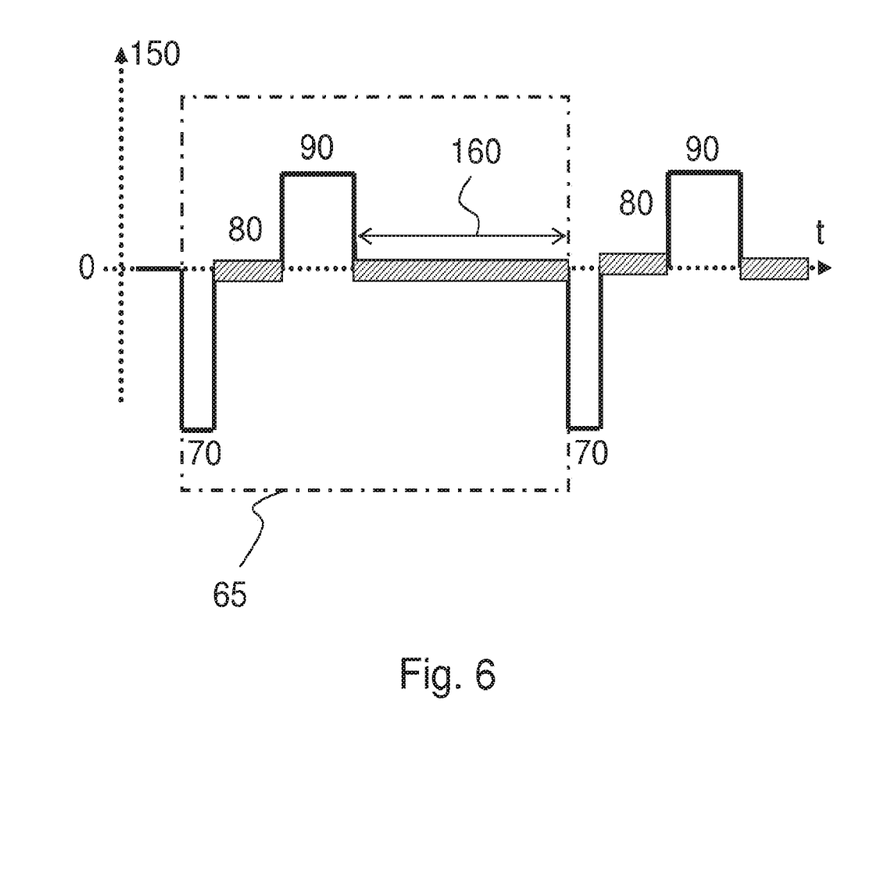
FIG. 6 shows an example of composition releasing sequence at the working electrode with respect to the reference electrode for releasing the composition according to the invention.

FIG. 6 shows an example of composition releasing sequence 65 that can be obtained at the working electrode 30 for releasing the composition according to the invention. More precisely, FIG. 6 shows the time evolution of the electrical potential of the working electrode 30 during a composition releasing sequence 65 with respect to the electrical potential of the reference electrode 60 (the abscissa 't' in FIG. 6 stands for time). Hence, a zero value of the electrical potential 150 is equal to the electrical potential 150 of the reference electrode 60 in this figure. In the example shown in FIG. 6, it is assumed that the first 70 and second 90 voltametric pulses have a square shape. Other shapes are nevertheless possible: as an example, pulses having triangular shapes can be used. The first 70 and second 90 voltametric pulses are separated by a rest period 80 during which the electrical voltage of the working electrode 30 with respect to the reference electrode 60 is unknown. A composition releasing sequence 65 finally comprises an intermediate period 160 at the end of which another composition releasing sequence 65 may be applied. Both rest 80 and intermediate 160 periods correspond to time durations during which no current is able to flow through the working electrode 30 and to time durations where electrical potential of the working electrode 30 is unknown and not actively applied.

During the first duration of the first voltametric pulse 70, the composition included in the electroactive conjugated polymer 40 is released. In the example of FIG. 6, it is assumed that a reduction of the electroactive conjugated polymer 40 allows a release of the composition. Hence, the voltage applied to the working electrode 30 during the first voltametric pulse 70 is negative with respect to the reference electrode 60. A release of a composition included in an electroactive conjugated polymer 40 after its oxidation (positive first voltametric pulse 70 in this case) is nevertheless possible for some compounds. In both cases, the applied voltage is optimized for an efficient release of the target compound or composition. After the release of the composition, it is desired not to re-attract it towards the working electrode 30 such that it can diffuse towards and/or into a zone of interest. Therefore, according to the invention, the composition releasing sequence 65 comprises a rest period 80 before a second voltametric pulse 90 is applied. During this second voltametric pulse 90, ions of the composition having diffused towards a targeted zone are replaced by others, but similarly charged, ions that are attracted towards the working electrode 30 because of the application of the second voltametric pulse 90. The voltage of this second voltametric pulse 90 is optimized for efficient replacement of the composition by a selected ion in the surrounding solution. When the three electrodes (30, 50, and 60) are implanted in living tissues, the ions allowing an efficient replacement of the composition are often chloride ions.

The durations of the first voltametric pulse 70, of the rest period 80, of the second voltametric pulse 90 and of the intermediate period 160 can be different. During the first voltametric pulse 70, the electroactive conjugated polymer 40 is reduced (negative voltage of the first voltametric pulse 70) or oxidized (positive voltage of the first voltametric pulse 70) depending on its electrochemical properties. Preferably, the first voltametric pulse 70 has a first duration equal to or shorter than 1 s. For example, for in vivo applications using electrode contacts of about 0.5 $mm^2$, when an electrical current of 100 µA is measured during the first voltametric pulse 70, flowing through the working 30 electrode, the first duration of the first voltametric pulse 70 is preferably chosen equal to or shorter than 100 µs. That means that the corresponding amount of delivered electrical charges is lower than or equal to 10 nC. Such a low value does not normally induce a stimulation of surrounding nerves or living tissues. In fact, if it is desired to prevent any stimulation of tissues surrounding the working electrode 30 during the first voltametric pulse 70, the quantity of delivered electric charges during this first voltametric pulse 70 should be kept lower than 65 nC. The optimal duration of the rest period 80 depends on the used electroactive conjugated polymer 40 and composition, and on environment in contact with the working electrode 30. Preferably, the rest period 80 is shorter than 10 ms but longer than 35 µs. During this rest period 80, the composition can diffuse in a targeted zone (living tissues as an example). Preferably, the second duration of the second voltametric pulse 90 is automatically determined from the quantity of flowing electrical charges between the working 30 and counter 50 electrodes during the first voltametric pulse 70 that is determined by the determination means 110. It is preferably desired to recover during the second voltametric pulse 90 the same amount of electric charges as the quantity of electrical charges delivered during the first voltametric pulse 70. Preferably, the duration of the second voltametric pulse 90 is equal or lower than 1 s. Preferably, an electrical current flowing through the working electrode 30 is measured during the second voltametric pulse 90 so that same electric charge as delivered electric charge during the first voltametric pulse 70 is recovered.

The magnitude of the voltage applied to the working electrode 30 during the first voltametric pulse 70 depends on the optimal voltage allowing an efficient release of the composition included in the electroactive conjugated polymer 40. Such a value can be determined by observing the oxydo-reduction peaks of the electroactive conjugated polymer 40 measured with a cyclic voltametry method as an example. Generally, the magnitude of the voltage at the working electrode 30 with respect to the reference electrode 60 during the first voltametric pulse 70 is comprised between −1 V and 0 V for most electroactive conjugated polymers 40. Preferably, such a magnitude is equal to −0.45 V referred to Silver/Silver Chloride or −0.61 V referred to Platinum for Dexamethasone loaded Polypyrrole. When a reduction process of the electroactive conjugated polymer 40 allows a release of a composition, the voltage applied at the working electrode 30 with respect to the reference electrode 60 during the first voltametric pulse 70 is negative. This allows a release of a composition that comprises negative ions. Then, the second voltametric pulse 90 has a positive polarity. The voltage magnitude of the second voltametric pulse 90 preferably corresponds to the electrochemical potential of the replacement ions (Chloride for instance). The magnitude of the second voltametric pulse 90 is preferably chosen such that maximum oxidation (or reduction) of the electroactive conjugated polymer 40 takes place during this second voltametric pulse 90. When the electroactive conjugated polymer 40 is Dexamethasone loaded polypyrrole, such a magnitude is preferably chosen between 0 V and 1 V. More preferably, this magnitude is equal to 0.3 V referred to silver/silver chloride or 0.14 V referred to platinum. When the composition comprises positive ions, the first polarity of the first voltametric pulse 70 is positive with respect to the reference electrode 60. The second voltametric pulse 90 has then a negative polarity preferably corresponding to the electrochemical potential of the replacement ions (potassium for instance).

As explained in the previous paragraph, the voltage to apply during the first voltametric pulse 70 is predetermined by the composition to release and by the electroactive conjugated polymer 40; the electric current between the working 30 and counter 50 electrodes during same first voltametric pulse 70 depends on the impedance between these two electrodes that cannot be adjusted. Thus, the duration of the first voltametric pulse 70 is used to control the amount of delivered electrical charges during the first voltametric pulse 70. For in vivo applications, this amount is chosen to be less than a threshold (around 65 nC typically) corresponding to a possible stimulation of tissues surrounding the working electrode 30. The quantity of composition that is released is directly proportional to the duration of the first voltametric pulse 70, i.e to the electric charges that are delivered at the working electrode 30.

Figure 7:
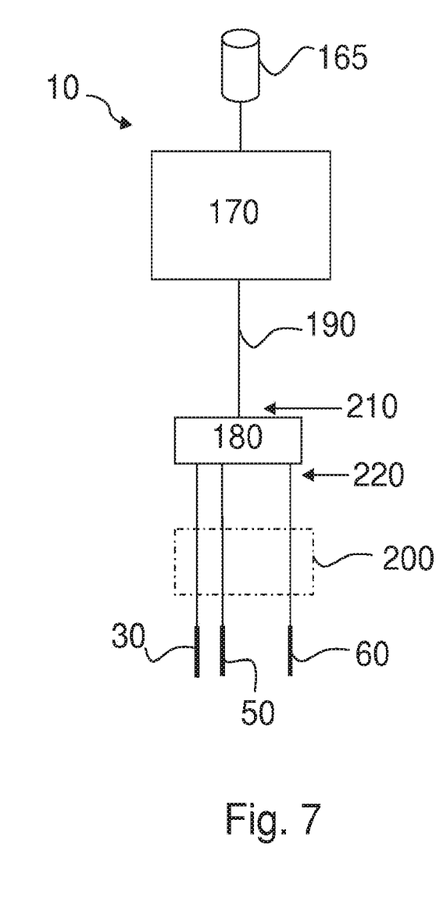
FIG. 7 shows another preferred example of electrical means for obtaining at least one composition releasing sequence at the working electrode.

FIG. 7 shows another example of electrical means for obtaining at the working electrode 30 at least one composition releasing sequence 65 such the one shown in FIG. 6. A control unit 170 such as a computer is able to send instructions and electric power from a battery 165 to an electronic housing 180 through a USB cable 190 as an example. The electronic housing 180 has a set of inputs 210 and a set of outputs 220. These outputs 220 are connected to the working 30, counter 50 and reference 60 electrodes through cables 200. Preferably, these cables 200 are shielded cables. When the control unit 170 is a computer, it preferably comprises a software module comprising processing data such as the voltage to apply during the first voltametric pulse 70 to have an optimal release of the composition, the optimal duration of the rest period 80 to have maximum diffusion for different compositions and the optimal second voltametric pulse 90 to restore the electroactive conjugated polymers 40 by preferably replacing the composition by suitable different ions. This software module preferably also comprises instructions for controlling a switch 100 for instance in order to produce the composition releasing sequence 65. In a preferred embodiment, the device 10 is implantable and can be implanted for instance in a mammal body. The control unit 170 is preferably a microprocessor that can function autonomously. In still another preferred embodiment, the implant can be miniaturized to the extreme such that the electrodes 30, 50, and 60 are controlled and powered by telemetry through the skin. In such an embodiment, the control unit 170 and the battery 165 are not implanted and the USB cable 190 does not exist. The reduced implanted electronic housing 180 would then be integrated with the electrodes 30, 50, and 60. In a preferred embodiment, in case the device 10 is implantable, it features a battery-based power source with either a primary cell or rechargeable battery. Programmed data (for instance pulse characteristics and regimen) can be either preset or wirelessly transmitted to the device 10 through a skin of a mammal body and the device 10 preferably features a small local microprocessor to process the data. The device electronics, ultra-low power and compact, is then preferably encapsulated in a biocompatible material with some proper means to connect to the three electrodes (30, 50, 60).

Figure 8:
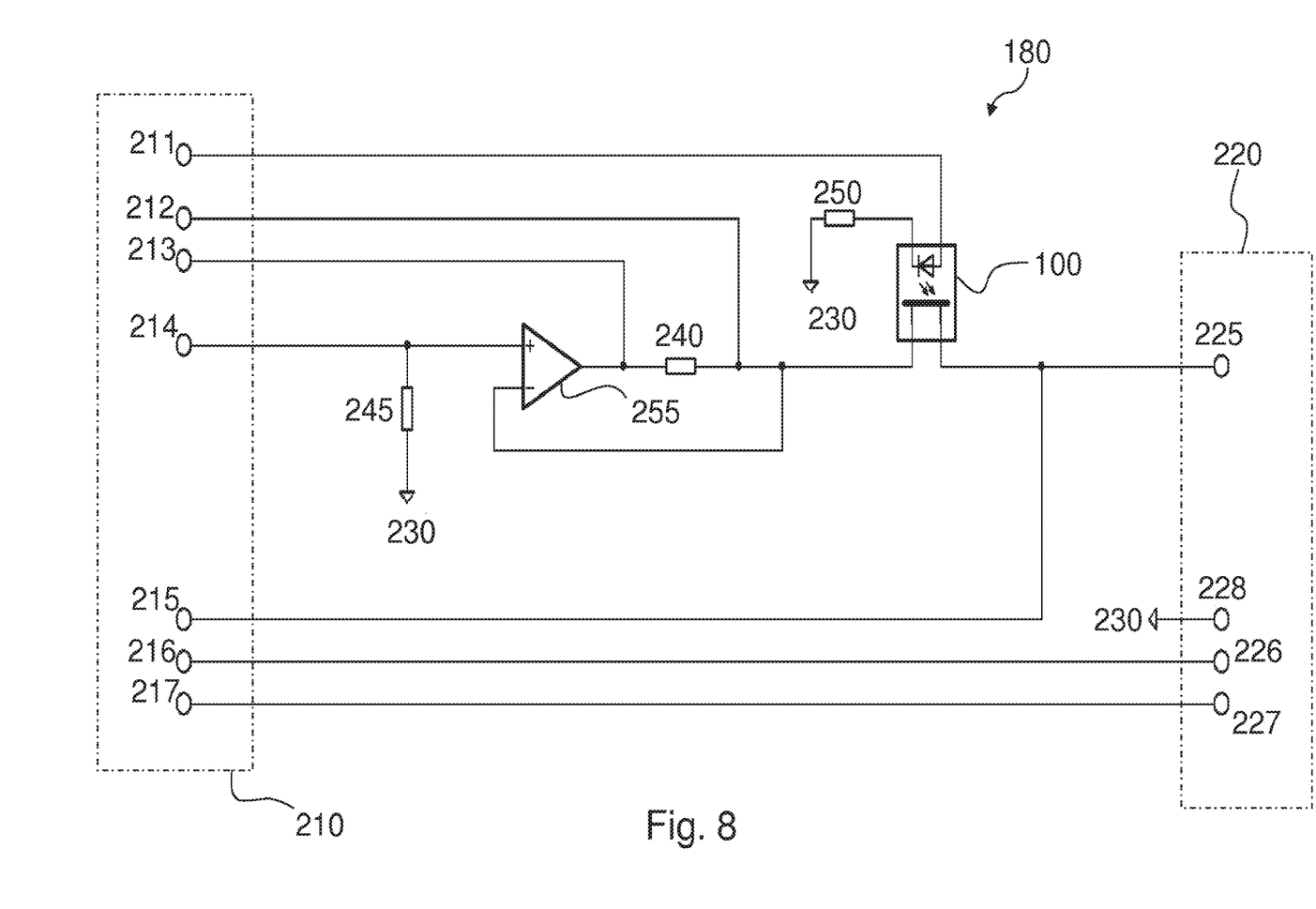
FIG. 8 shows an example of electronic circuit of a preferred embodiment of the electrical means.

FIG. 8 shows a preferred example of electronic circuit of the electronic housing 180 for the preferred embodiment shown in FIG. 7. The working electrode 30 is connected to the output 225, and the counter electrode 50 is connected to output 228 that is connected to ground 230. Input 215 allows measuring the electric potential of the working electrode 30. It the example shown in FIG. 8, it is assumed that there are two reference electrodes 60. For biocompatible reasons, it is preferred to use titanium or platinum for the reference electrode 60 as an example. However, such an electrode can present a varying electric potential because of various physical effects, such as a variation in temperature. By using two reference electrodes 60 and by comparing the stability of their electric potential (thanks to inputs 216 and 217), one can calculate an ideal reference potential from the variable reference electrode 60 potential. Such two or more reference electrodes are connected to outputs 226 and 227 of FIG. 8. Inputs 216 and 217 are preferably connected to a control unit 170 to check the electric potential of these two reference electrodes 60. The switch 100 of FIG. 8 is controlled by a digital input 211. In FIG. 8 the switch 100 is assumed to be an optocoupler (or optoisolator). This switch 100 is closed during the first 70 and second 90 voltametric pulses, whereas it is open during the rest period 80 and during the intermediate period 160 between two composition releasing sequences 65. When the switch 100 is open, there is zero current flow through the working electrode 30 (or said in an equivalent manner, no current is able to flow through the working electrode 30). Hence, the switch 100 allows imposing that no current is able to flow through the working 30 electrode during the rest period 80 and during the intermediate period 160 between two composition releasing sequences 65. An analog input 214 allows fixing the voltage values of the first 70 and second 90 voltametric pulses with respect to the reference electrode 60. For the composition releasing sequences 65 shown in FIG. 6, this voltage value is negative (respectively positive) during the first 70 (respectively second 90) voltametric pulse. As shown in FIG. 8, there are also an operational amplifier 255 and different resistors 240, 245, and 250. Preferably, the resistors 240 and 245 have an electric resistance of 1 kOhm. Preferably, the resistor 250 has an electric resistance of 100 Ohms. By measuring the difference between the electrical potentials of inputs 213 and 212, one can deduce the electrical current flowing through the output 225 when the switch 100 is closed (as the value of the resistor 240 is known). As an alternative of the situation described in FIG. 8, the electrical current that is delivered can be measured on a resistor inserted between 228 and 230. In this case, the measurement would be referred to the ground but this is only possible when a single drug releasing channel is used because multiple channel systems would use a common counter electrode 50. A measure of this electric current flowing during the first voltametric pulse 70 is important because this measurement should allow one to determine the duration of the second voltametric pulse 90. Indeed, as an electric current is a measure of the number of electric charges carried per unit time, it is then possible to deduce the number of electric charges delivered if one knows the electric current flowing through the working electrode 30 and the duration during which such a current flows. This is done by time integration of this electric current during the first duration of the first voltametric pulse 70. Knowing the number of electric charges delivered during the first voltametric pulse 70, one has to adapt the second duration of the second voltametric pulse 90 so that the amount of electric charges recovered during the second voltametric pulse 90 compensates the quantity of electric charges delivered during the first voltametric pulse 70.

Figure 9:
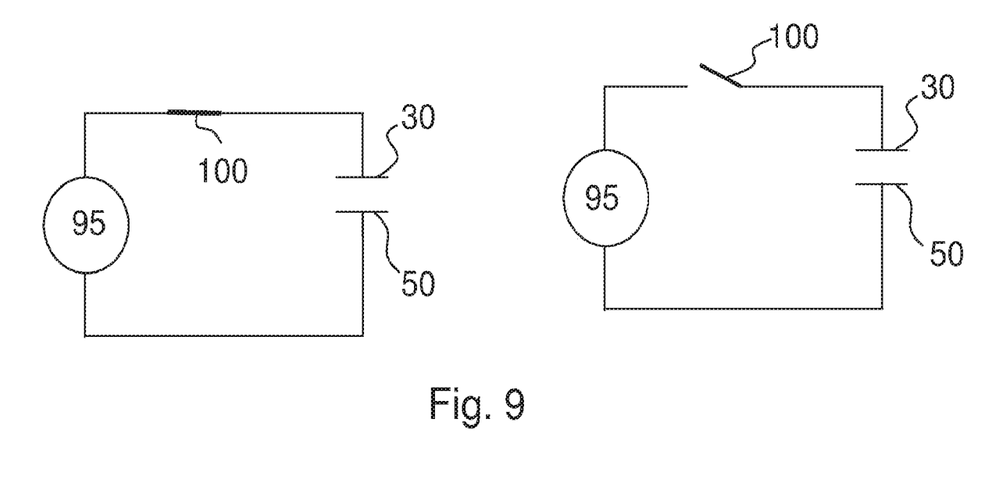
FIG. 9 shows a simplified illustration of the circuit configuration for the device of the invention when the electrical means comprise a voltage source.
Figure 10:
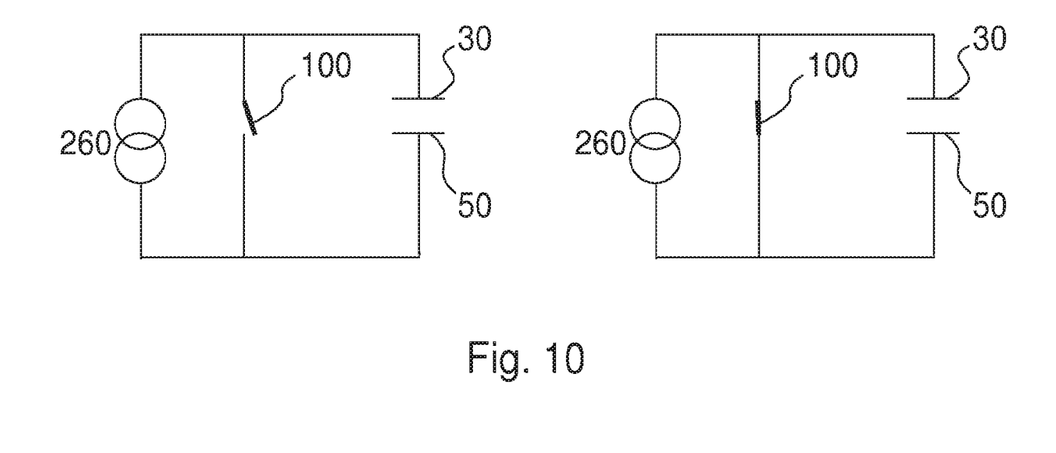
FIG. 10 shows a simplified illustration of the circuit configuration of a solution known in the state of the art.

As illustrated in FIG. 8, during the intermediate period 160 between two composition releasing sequences 65, the electrical circuit imposes that no current is able to flow through the working electrode 30 connected to output 225. Such a configuration is different from the solution proposed in FIG. 1 of the article entitled "Promoting neurite outgrowth from spiral ganglion neuron explants using polypyrrole/BDNF-coated electrodes" by Evans A J et al. and published in J Biomed Mater Res A. 2009 October; 91 (1):241-50. In this publication, the intermediate period between two biphasic current pulses correspond to a short-circuit phase. FIG. 9 presents a simplified view of the circuit configuration for the invention when the electrical means comprise a voltage source 95, whereas FIG. 10 presents a simplified view of the circuit configuration for the solution proposed in afore-mentioned publication. These figures are only shown for explaining the differences between the invention and the set-up of Evans A J et al's article when a a voltage source 95 is used for the device 10 of the invention. Hence, these figures do not relate to real circuit implementations. The circuits on the left parts correspond to the periods during which voltage (FIG. 9) or current (FIG. 10) pulses takes place at the working electrode 30. The circuits on the right parts correspond to the intermediate periods during which no pulse is applied to the working electrode 30. In FIG. 10, the electrodes 30 and 50 are connected to a current source 260 and during the intermediate period, there is a short-circuit configuration as explained in page 243 of the afore-mentioned article. The solution proposed in the invention and as illustrated in FIG. 9 allows a better control of release of a composition compared to the solution proposed in the afore-mentioned publication, notably allowing avoiding such a release when it is not desired (passive release) thanks to imposing zero current through the working electrode 30 as illustrated in the right part of FIG. 9. For the device 10 of the invention, an open-circuit configuration (zero current) is indeed imposed during the rest period 80 as well as during an intermediate period 160 between two composition releasing sequences 65. Hence, even if electrical charges have been accumulated in a living tissue for instance, the open-circuit configuration (zero current) (imposed by the switch 100 in the example shown in FIG. 9) prevents these charges from flowing during the rest period 80 as well as during an intermediate period 160 through the working electrode 30.

As explained above, in a preferred embodiment, the electrodes 30, 50, 60, the switch 100, and a voltage source 95 are implanted in a human or animal body. Biocompatible wires then connect this voltage source 95 to the working electrode 30 via the switch 100. In such an embodiment, the switch 100 can be remotely activated so that the release of a composition can be initiated or interrupted without the need of surgical procedures. A control unit 170 and electronic housing 180 are also preferably implanted is such a case.

In another preferred embodiment, the device 10 comprises several working electrodes 30 for delivering a same composition at different places or for delivering different types of composition. In the latter case, the different working electrodes 30 are preferably controlled separately, and the controlled signals applied to them are preferably adjusted to allow an optimal release of the corresponding composition. In such an embodiment, the device 10 can comprise only one counter electrode 50 if each channel has an independent current measuring resistor 240, for example as represented in FIG. 8. One or more reference electrodes 60 can be used.

Preferably, the first duration of the first voltametric pulse is such that it prevents said first voltametric pulse from inducing a stimulation of nerves and/or living tissues. In another preferred embodiment, the electrical means for obtaining at the working electrode 30 the at least one composition releasing sequence 65 are also able to produce at the working electrode 30 an output appropriate for stimulating nerves or living tissues. Then, the device 10 of the invention can be used both for delivering a composition and for stimulating nerves or living tissues. In this last preferred embodiment, the electrical means are able to produce at the working electrode 30 an output appropriate for stimulating nerves or living tissues preferably when the composition is totally released. However, in other preferred embodiments, stimulations of nerves or living tissues could take place concurrently to the release of the composition. Preferably, the same voltage 95 or current 260 sources and the same controller 300 and same control unit 170 are used for delivering the composition and for stimulation nerves or living tissues when the device 10 of the invention is used both for delivering a composition and for stimulating nerves or living tissues. However, the device 10 could comprise specific stimulation means for producing at the working electrode 30 an output appropriate for stimulating nerves or living tissues; that means that specific stimulation means, different from the electrical means used for lectrochemically releasing a composition, could be used in this preferred embodiment.

Preferred Experimental Details a) Preparation of the Working Electrode 30
The working electrode 30 is preferably electrochemically prepared. The elaboration consists in coating a thin polymer film on the said working electrode 30, which contains at least one surface made of metal. For that, a classical three electrode set up is used. The working electrode 30, a reference electrode 60, and a counter-electrode 50 are immersed in a solution containing the monomer and an electrolytic salt comprising at least the composition to release. The polymer coating on the working electrode 30 is preferably made by oxidizing the monomer. During the polymerization, the composition is incorporated within the polymer as counter-ion.

b) In-Vitro Composition Release
The active release of the composition from the working electrode 30 coated with the polymer is then electrochemically performed. For that, a classical three electrode set up is used. The working electrode 30, a reference electrode 60, and a counter electrode 50 are immersed in saline bath as electrolytic bath to approximate in-vivo conditions. Voltage cycles are then preferably applied to the working electrode 30.

c) In-Vitro Release Monitoring
Monitoring the release is preferably carried out by removal of the electrolytic solution, using a method of characterization depending upon the nature of the composition.

According to a second aspect, the invention relates to a method a method for a controlled electrochemical release of a composition from at least one working electrode 30 comprising an electroactive conjugated polymer 40 containing or doped with said composition, said method comprising the step of imposing between the at least one working electrode 30 and a counter electrode 50 specific electrical conditions for obtaining at said at least one working electrode 30 at least one composition releasing sequence 65 with respect to a reference electrode 60, each composition releasing sequence 65 comprising:
  i) a first voltametric pulse 70 for releasing said composition and having a first voltage, a first duration and a first polarity, followed by
  ii) a rest period 80 during which no current is able to flow through said working electrode 30, followed by
  iii) a second voltametric pulse 90 for replacing said composition with at least one ion, having a second voltage, a second duration and a second polarity opposite to the first polarity, followed by
  iv) an intermediate period 160 during which no current is able to flow through said at least one working electrode 30, at the end of which another composition releasing sequence 65 may be applied.

Preferably, a quantity of electrical charges flowing through said working electrode 30 during step i) is determined. More preferably, a quantity of electrical charges flowing through said working electrode 30 during step iii) is determined.

Preferably, the number of composition releasing sequences 65 is adapted for releasing a preset quantity of composition. More preferably, the frequency of composition releasing sequences 65 is adapted for releasing a quantity of composition at a preset rate.

The present invention has been described in terms of specific embodiments, which are illustrative of the invention and not to be construed as limiting. More generally, it will be appreciated by persons skilled in the art that the present invention is not limited by what has been particularly shown and/or described hereinabove. The invention resides in each and every novel characteristic feature and each and every combination of characteristic features. Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

Summarized, the invention may also be described as follows. According to a first aspect, the invention relates to a device 10 for electrochemically releasing a composition and comprising: one working electrode 30 comprising an electroactive conjugated polymer 40 containing or doped with said composition, a counter electrode 50, and a reference electrode 60. The device 10 of the invention is characterized in that it comprises electrical means (95, 100; 320; 165, 180) connected to the working electrode 30 and to the counter electrode 50 for obtaining at said working electrode 30 at least one composition releasing sequence 65 with respect to said reference electrode 60, each composition releasing sequence 65 comprising: a first voltametric pulse 70, followed by a rest period 80 during which no current is able to flow through said working electrode 30, followed by a second voltametric pulse 90, followed by an intermediate period 160 during which no current is able to flow through said working electrode 30. According to a second aspect, the invention relates to a method for electrochemically releasing a composition.

The following numerals have been used:
"10" The device of the invention
"30" The working electrode
"40" The electroactive conjugated polymer
"50" The counter electrode
"55" Amplifier
"60" The reference electrode
"65" Composition releasing sequence
"70" The first voltametric pulse during which the composition is released
"80" The rest period between the voltametric pulses
"90" The second voltametric pulse during which the composition is replaced
"95" Voltage source
"100" Switch
"110" Means for measuring an electric current between the working electrode "30" and the counter "50" electrode
"120" Polypyrrole oxidized conductive form
"130" Polypyrrole neutral form
"140" Nanoscopic sized electrically conducting surface microstructures
"160" Intermediate rest period
"165" Battery
"170" Control unit (ex: Computer)
"180" Electronic housing
"190" USB cable
"200" Cables
"210" ("211" to "217") Electronic housing inputs
"220" ("225" to "228") Electronic housing outputs
"230" Ground
"240" Resistor
"245" Resistor
"250" Resistor
"255" Operational amplifier
"260" Current source
"300" Controller
"310" Amplifier
"320" Current source These numerals cannot be interpreted as limiting and are mentioned for information purpose only.

What is claimed is:

1. A device for a controlled electrochemical release of a composition, comprising:
at least one working electrode comprising an electroactive conjugated polymer containing or doped with said composition;
a counter electrode;
a reference electrode;
electrical circuitry connected to the at least one working electrode and to the counter electrode and configured to perform at least one composition releasing sequence between the working electrode and the reference electrode by
applying a first voltametric pulse having a first voltage, a first polarity and a first duration, the first voltametric pulse being configured to release the composition, followed by a rest period during which no current is able to flow through said at least one working electrode, followed by a second voltametric pulse having a second voltage, a second polarity opposite to said first polarity and a second duration, the second voltametric pulse being configured to replace the composition with at least one ion, followed by an intermediate period during which no current is able to flow through said at least one working electrode.

2. The device of claim 1, wherein said electrical circuitry comprises a voltage source and a switch connected between the at least one working electrode and the counter electrode.

3. The device of claim 1, wherein said electrical circuitry comprises a current source connected between the at least one working electrode and the counter electrode.

4. The device of claim 1, wherein said rest period has a duration in the range of 35 µs to 10 ms.

5. The device of claim 1, further comprising an ammeter configured to determine a quantity of flowing electrical charges through the at least one working electrode during the first and second voltametric pulses.

6. The device of claim 1, further comprising a time integrator configured to adapt the first duration of the first voltametric pulse for allowing the device to release a preset quantity of composition.

7. The device of claim 1, further comprising a time integrator configured to automatically determine and adapt the second duration of the second voltametric pulse from a quantity of flowing electrical charges through the at least one working electrode during the first voltametric pulse.

8. The device of claim 1, wherein the first duration of the first voltametric pulse is such that no stimulation of nerves and/or living tissues can be induced during this first voltametric pulse.

9. The device of claim 1, further comprising stimulation circuitry configured to produce at the at least one working electrode an output appropriate for stimulating nerves or living tissues.

10. The device of claim 9, wherein said stimulation circuitry is configured to produce at the at least one working electrode an output appropriate for stimulating nerves or living tissues when the composition is totally released.

11. A method for a controlled electrochemical release of a composition from at least one working electrode comprising an electroactive conjugated polymer containing or doped with said composition, said method comprising:
imposing between the at least one working electrode and a counter electrode specific electrical conditions for obtaining at said at least one working electrode at least one composition releasing sequence with respect to a reference electrode, each composition releasing sequence comprising:
a first voltametric pulse for releasing said composition and having a first voltage, a first duration and a first polarity, followed by a rest period during which no current is able to flow through said at least one working electrode, followed by a second voltametric pulse for replacing said composition with at least one ion, having a second voltage, a second duration and a second polarity opposite to the first polarity, followed by an intermediate period during which no current is able to flow through said at least one working electrode, at the end of which another composition releasing sequence may be applied.

12. The method of claim 11, further comprising determining a quantity of electrical charges flowing through said at least one working electrode during the first voltametric pulse.

13. The method of claim 11, further comprising determining a quantity of electrical charges flowing through said at least one working electrode during the second voltametric pulse.

14. The method of claim 11, wherein the number of composition releasing sequences is adapted for releasing a preset quantity of composition.

15. The method of claim 11, wherein the frequency of composition releasing sequences is adapted for releasing a quantity of composition at a preset rate.

* * * * *